(12) United States Patent
Meyers

(10) Patent No.: US 8,477,036 B2
(45) Date of Patent: Jul. 2, 2013

(54) PATIENT SUPPORT INTERFACE PRESSURE MONITORING SYSTEM

(76) Inventor: Clarissa A. Meyers, McAllen, TX (US)

(*) Notice: Subject to any disclaimer, the term of this patent is extended or adjusted under 35 U.S.C. 154(b) by 6 days.

(21) Appl. No.: 12/799,543

(22) Filed: Apr. 24, 2010

(65) Prior Publication Data

US 2011/0264007 A1 Oct. 27, 2011

(51) Int. Cl.
G08B 23/00 (2006.01)
(52) U.S. Cl.
USPC ............... 340/573.1; 34/573.7; 600/587
(58) Field of Classification Search
USPC ...... 600/587, 595; 340/573.1, 573.7; 382/115
See application file for complete search history.

(56) References Cited

U.S. PATENT DOCUMENTS

| | | | |
|---|---|---|---|
| 7,027,358 B1* | 4/2006 | Esposito et al. | 600/587 |
| 2004/0111045 A1* | 6/2004 | Sullivan et al. | 600/595 |
| 2005/0172398 A1* | 8/2005 | Smith et al. | 340/573.1 |
| 2008/0181465 A1* | 7/2008 | Sauerwein | 382/115 |
| 2010/0298742 A1* | 11/2010 | Perlman et al. | 600/595 |

OTHER PUBLICATIONS

Nishida et al., Monitoring Patient Respiration and Posture Using Human Symbiosis System, 1997, Proceedings of the 1997 IEEE/RSJ International Conference on Intelligent Robots and Systems, vol. 2, pp. 632-639.*

* cited by examiner

Primary Examiner — Brian Szmal
Assistant Examiner — Emily Lloyd
(74) Attorney, Agent, or Firm — Wayne J. Colton, Inc.

(57) ABSTRACT

An interface pressure monitoring system includes an underlayment interposed between a patient support surface and a patient supported thereon and a processor. The underlayment includes pressure sensors such as, for example, an array of piezoelectric pressure sensors. The processor acquires pressure data from the underlayment, analyzes the data and stores the analyzed data for further processing, alerting and/or reporting.

21 Claims, 9 Drawing Sheets

PATIENT SUPPORT INTERFACE PRESSURE MONITORING SYSTEM

FIELD OF THE INVENTION

The present invention relates to patient care. More particularly, the invention relates to a system and method for monitoring, mapping and tracking over time the interface pressures produced between a surface and patient supported thereon, the system being specifically adapted to alert the patient or a caregiver of a need for repositioning in prevention and/or treatment of tissue damage.

BACKGROUND OF THE INVENTION

Figure 1:
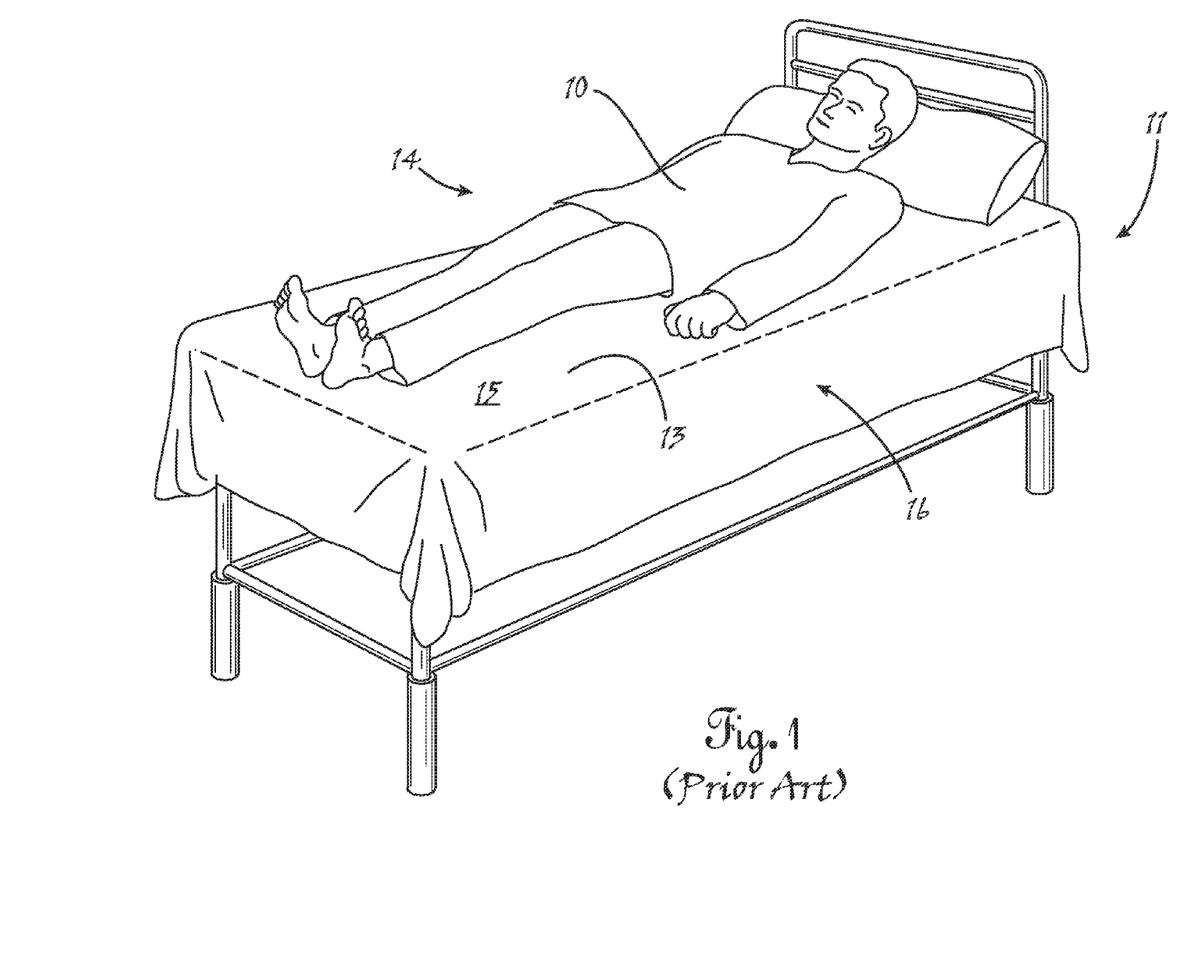
FIG. 1 shows, in a perspective view, a patient as confined to bed in a supine position.
Figure 3:
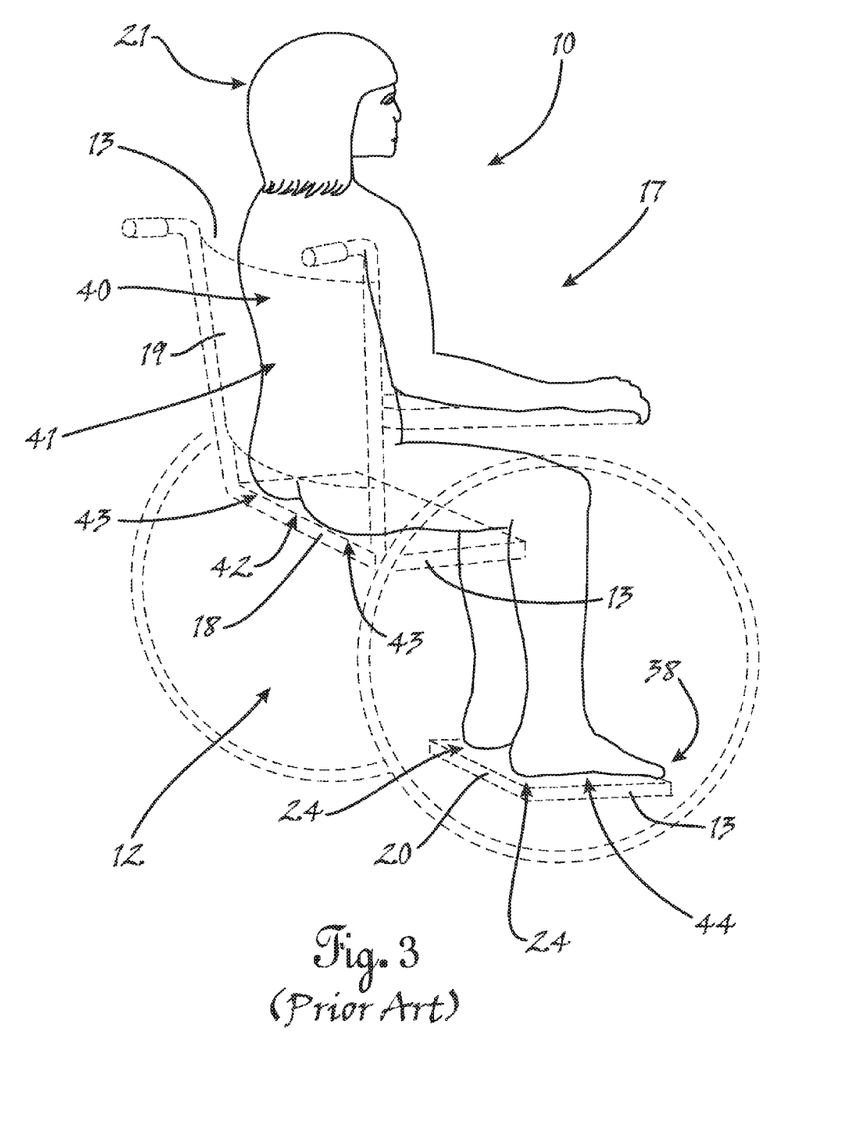
FIG. 3 shows, in a perspective view, a patient as confined to a wheelchair in a sitting position, the figure showing also the prevalent locations for the formation of decubitus ulcers, or pressure sores, in a patient so confined.

As a result of disease, surgery, age, injury or other infirmity, many patients 10 suffer such decreased mobility as to become generally confined to a bed 11, as depicted in FIG. 1, or a wheelchair 12, as depicted in FIG. 3. As particularly shown in the figures, such a patient 10 is generally immobilized in a fixed position atop and/or about one or more patient support surfaces 13. For example, the patient 10 as depicted in FIG. 1 is shown to be immobilized in a supine position 14 supported on the top surface 15 of a mattress 16 while the patient 10 as depicted in FIG. 3 is shown to be immobilized in a sitting position 17 supported on and about seat bottom 18, seatback 19 and footrest 20. In order to maximize comfort for such immobilized patients 10, the manufacturers of hospital type beds 11 and wheelchairs 12 go to great lengths for the development of advanced patient support surfaces 13, a particular goal of such manufacturers being minimization of localized interface pressures.

Figure 2A:
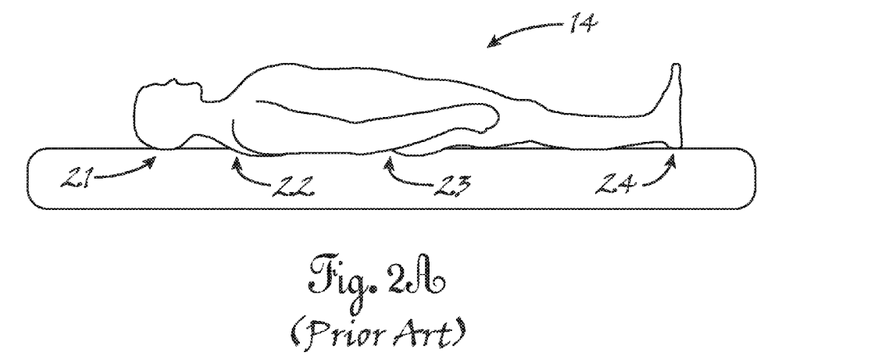
FIG. 2A shows, in a schematic diagram, the prevalent locations for the formation of decubitus ulcers, or pressure sores, in a patient confined for an excessive time to the supine position.

Unfortunately, and notwithstanding the best efforts to date of manufacturers, confined or otherwise immobile patients 10 remain dangerously susceptible to the hazards of elevated interface pressures, which pressures can within a very short period of time result in tissue breakdown leading to decubitus ulcers. In particular, as depicted in FIG. 2A, patients 10 confined to the supine position 14 are generally placed at heightened risk for the development of decubitus ulcers in the occipital region 21 about the occipital bone at the back of the patient's head; in the left and right scapular regions 22 about the patient's scapulae, or shoulder blades; in the sacral region 23 about the patient's sacrum at the lower end of the patient's vertebral column; and in the calcaneal, or calcanean, regions 24 about the patient's calcanei, or heels.

Figure 2B:
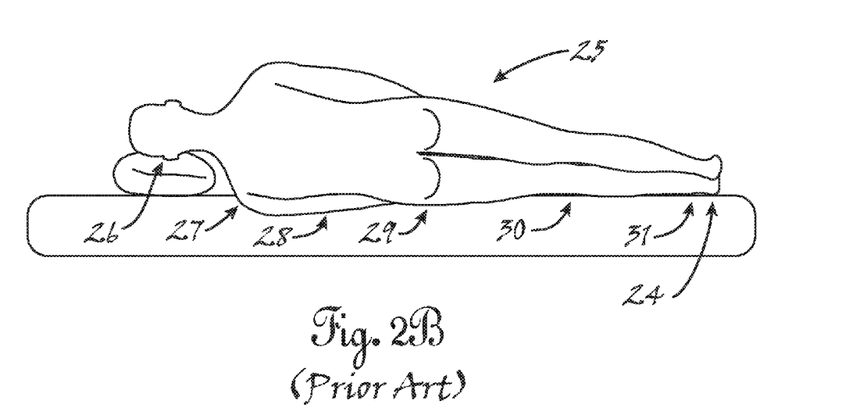
FIG. 2B, shows, in a schematic diagram, the prevalent locations for the formation of decubitus ulcers, or pressure sores, in a patient confined for an excessive time to a lateral position.

Likewise, as shown in FIG. 2B, patients confined in a left or right lateral position 25 are generally placed at heightened risk for the development of decubitus ulcers in the auricular regions 26 on or about the patient's lower auricle—the shell-like structure on the side of the head forming in part the external ear; in the acromial region 27 of the patient's lower acromion or acromial process, or "point of the shoulder;" in the cubital region 28 of the patient's cubitus, or elbow, underlying the patient; in the trochanteric region 29 of the patient's lower, greater trochanter at the upper extremity of the patient's femur; in the condylar regions 30 about the patients lateral and medial condyle of tibia to the sides of the patient's knees; in the malleolar regions 31 about the patient's lateral and medial malleoli, or ankles; and in the calcaneal, or calcanean, regions 24 about the sides of the patients calcanei, or heels.

Figure 2C:
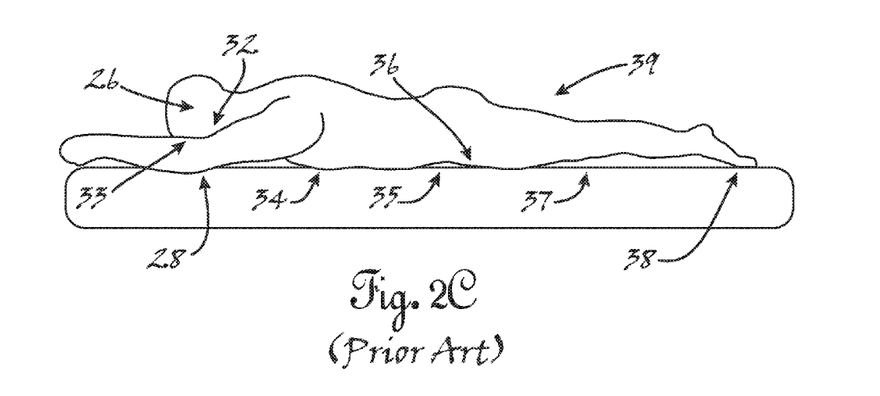
FIG. 2C shows, in a schematic diagram, the prevalent locations for the formation of decubitus ulcers, or pressure sores, in a patient confined for an excessive time to the prone position.

Still further, as shown in FIG. 2C, patients confined to the prone position 39 are generally placed at heighted risk for the development of decubitus ulcers in the cubital regions 28 of the patient's cubiti, or elbows; in the auricular regions 26 about the patient's auricles; buccal regions 32 about the patient's cheeks; in the nasal regions 33 about the patient's nasus, or external nose; in the pectoral regions 34 about the patient's breasts; in the case especially of a male patient, in the genital region 35 about the male patient's genitalia; in the iliac regions 36 about the patient's iliac crests (the broad, flaring portions of the hip bones); in the patellar regions 37 about the patient's patellae, or kneecaps; and in the pedal regions 38 about the patient's toes.

While generally more ambulatory than a bedridden patient 10, patients 10 confined to wheelchairs 12, as depicted in Figure 3, are nonetheless susceptible to decubitus ulcers. Additionally, because the confinement of many such patients 10 is concomitant diagnoses involving sensory degradation, such as, for example, spinal cord injuries and complications of diabetes, such patients 10 are often at increased risk because such patients 10 can easily develop an ulcer that is not detected by the patient 10 due to lack of sensation and is also not detected by a caregiver due to the relative independence of the patient 10. In any case, as shown in FIG. 3, patients 10 confined to the sitting position 17 are generally placed at heighted risk for the development of decubitus ulcers in the region 40 of the inferior angle patient's scapula; in the spinal regions 41 particularly about the patient's thoracic spine; the coccygeal region 42 about the patient's coccyx, or tailbone; in the ischial, or sciatic, regions 43 about the patient's ischial tuberosities, which are the main a weight-bearing points for a patient in the sitting position 17; in the plantar regions 44 about the plantar surfaces, or soles, of the patient's feet; in the calcaneal, or calcanean, regions 24 about the patient's calcanei, or heels; and in the pedal regions 38 about the patient's toes. In the case of a patient 10 so confined and also requiring a headrest or like support, the patient 10 is additionally susceptible to decubitus ulcers in the occipital region 21 about the occipital bone at the back of the patient's head.

Regardless of location, however, it should be understood that in addition to being extremely painful, any decubitus ulcer once formed is at best difficult and expensive to treat. Additionally, it should be clearly understood that treatment often fails, leading to rapid decline of the patient's health and ultimately, in many cases, to the patient's death and/or drastically increased costs and services. As a result, any advance in the prevention and treatment of decubitus ulcers should be regarded as addressing a longstanding, unsolved problem.

With the foregoing background in mind, it is therefore an overriding object of the present invention to advance the care afforded to patients vulnerable to the formation of decubitus ulcers. In particular, it is an object of the present invention to provide a system and method by which excessive interface pressures may be readily and robustly detected and, additionally, whereby the patient and/or patient's caregiver may be alerted to the need for repositioning in prevention or treatment of interface pressure related tissue damage. Additionally, it is an object of the present invention to provide such a system and method that may be readily utilized by skilled and unskilled caregivers alike. Further, it is an object of the present invention to provide such a system and method that also makes provision for review of the care afforded a patient, thereby not only ensuring that caregivers provide timely intervention in response to a detected dangerous situation but also providing a tool for use by a clinician evaluating the effectiveness of past care and need for adjustment to a treatment protocol.

SUMMARY OF THE INVENTION:

In accordance with the foregoing objects, the present invention—an interface pressure monitoring system—generally comprises an underlayment adapted to be interposed between a patient support surface and a patient supported thereon and a processor. The underlayment comprises a plurality of pressure sensors such as, for example, an array of piezoelectric pressure sensors. The processor acquires pressure data from the underlayment, analyzes the data and stores the analyzed data for further processing, alerting and/or reporting.

Finally, many other features, objects and advantages of the present invention will be apparent to those of ordinary skill in the relevant arts, especially in light of the foregoing discussions and the following drawings, exemplary detailed description and appended claims.

BRIEF DESCRIPTION OF THE DRAWINGS:

Although the scope of the present invention is much broader than any particular embodiment, a detailed description of the preferred embodiment follows together with illustrative figures, wherein like reference numerals refer to like components, and wherein.

DETAILED DESCRIPTION OF THE PREFERRED EMBODIMENT:

Although those of ordinary skill in the art will readily recognize many alternative embodiments, especially in light of the illustrations provided herein, this detailed description is exemplary of the preferred embodiment of the present invention, the scope of which is limited only by the claims appended hereto.

Figure 4:
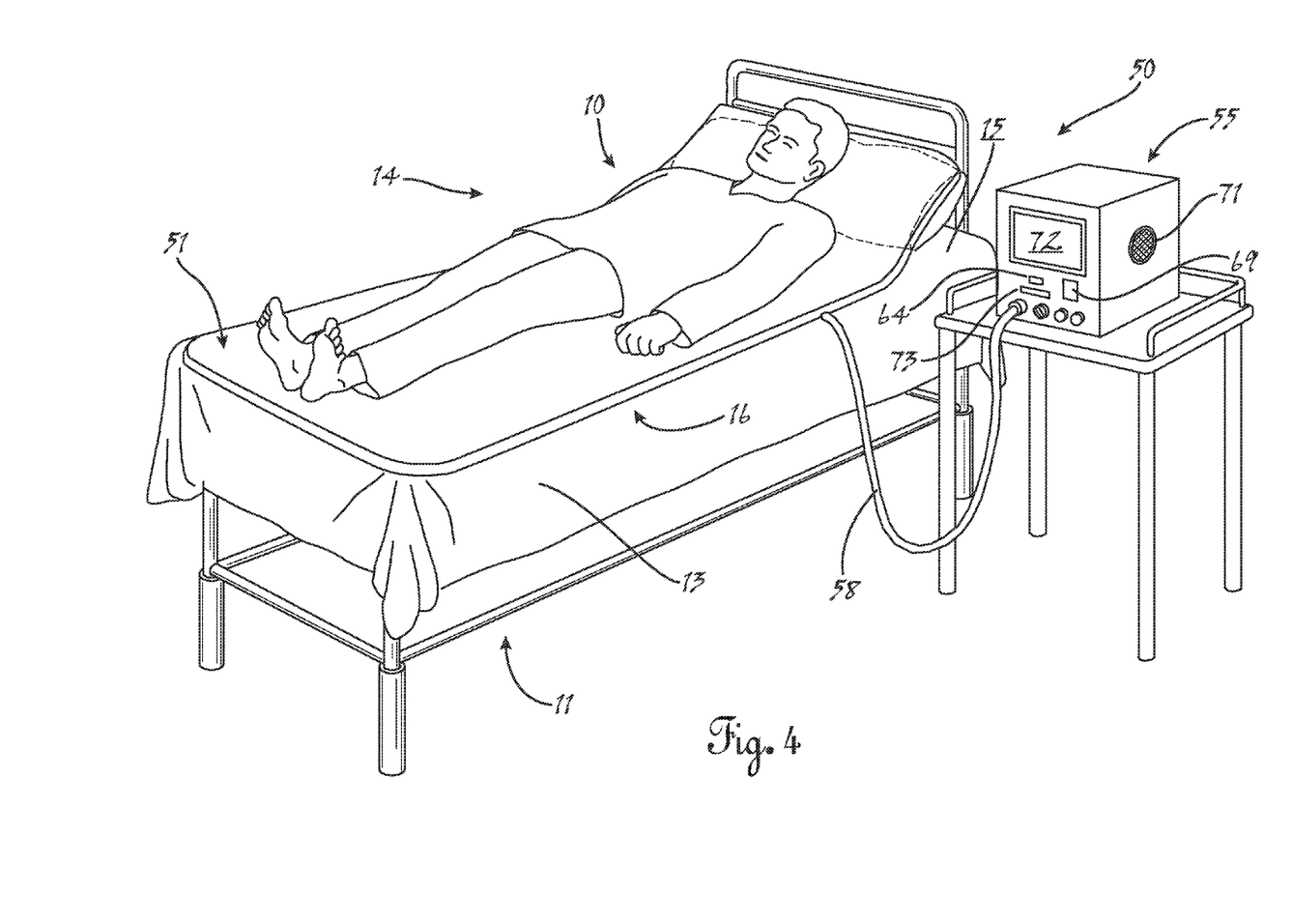
FIG. 4 shows, in a perspective view, the preferred embodiment of the interface pressure monitoring system of the present invention as deployed for use in connection with a patient confined to bed.
Figure 5:
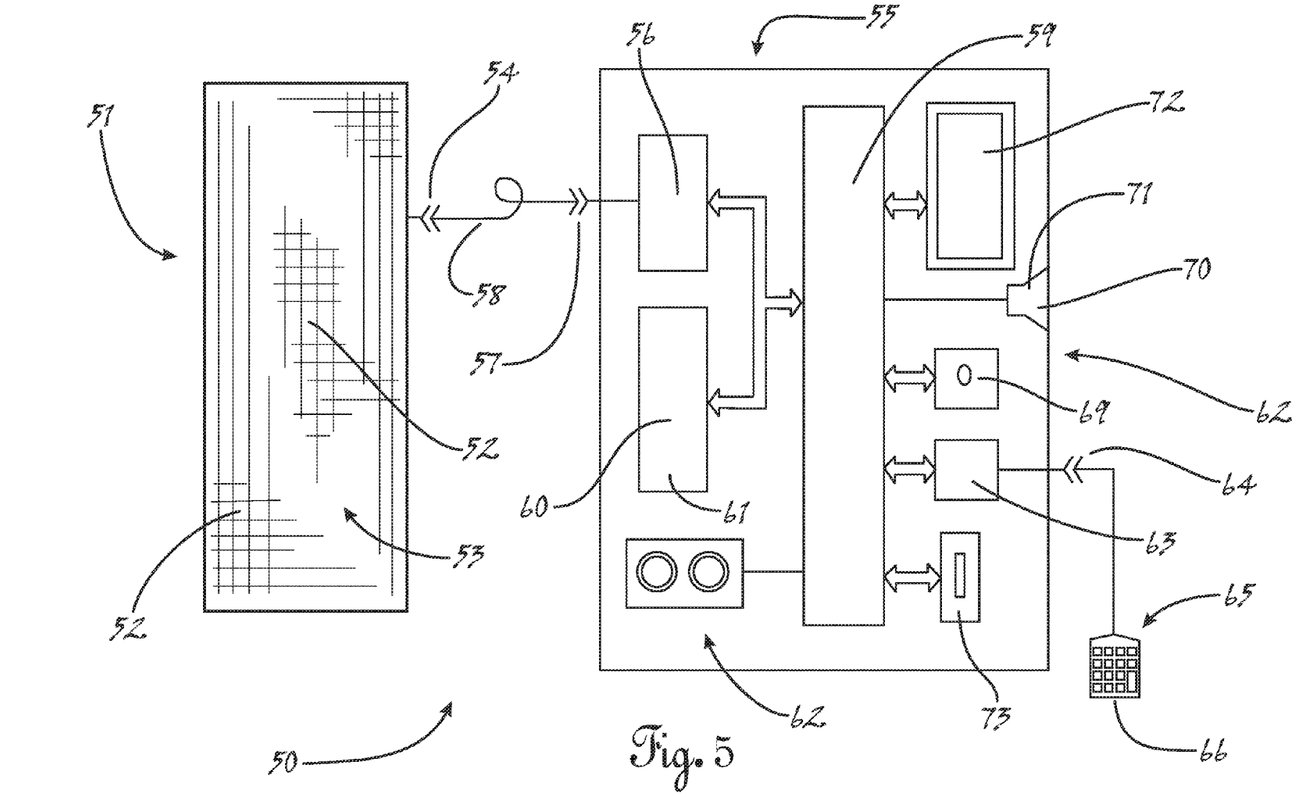
FIG. 5 shows, in a schematic block diagram, various details of the interface pressure monitoring system of FIG. 4.

Referring now to FIGS. 4 and 5 in particular, the interface pressure monitoring system 50 according to the preferred embodiment of the present invention is shown to generally comprises an underlayment 51 adapted to be interposed between a patient support surface 13 and a patient 10 supported thereon and a processor 55. As shown in FIG. 4, a suitable patient support surface 13 in connection with which the present invention may be utilized may comprise the top surface 15 of a mattress 16 of a bed or, as shown in FIG. 3, may comprise one or any combination of the seat bottom 18, the seatback 19 or the footrest 20 of a wheelchair or any other substantially equivalent patient surface. In any case, the underlayment 51 according to the present invention comprises a plurality of pressure sensors 52 such as, for example, an array 53 of piezoelectric pressure sensors. While such sensors are generally known to those of ordinary skill in the art, one example of an implementation that may be adapted to the teachings of the present invention is found in U.S. Pat. No. 6,720,712 B2 issued Apr. 13, 2004 to Scott et al. By this reference, the full disclosure of U.S. Pat. No. 6,720,712 B2 is incorporated herein as though now set forth in its entirety.

In any case, any appropriate cable 58 interconnects the electrical interface 54 from the pressure sensors 52 to the processor 55 through a provided electrical interface 57 to a data acquisition circuit 56 provided in connection with the processor 55. In the case of an implementation of a piezoelectric sensor array 53, the data acquisition circuit preferably provides the input signal generator and the output signal processor for the piezoelectric sensor array 53, thereby distributing this hardware away from the underlayment 51 and thus preventing the introduction of bulky and hard surfaces to the area where patient contact may occur.

The processor 55 further comprises a controller 59 and associated firmware and/or software, enabling the processor to be adapted for pressure data acquisition, analysis and storage as well as for alerting and reporting functions as will be better understood further herein. In order that the processor may store the acquired pressure data, however, a mass storage device 60 is provided. Although those of ordinary skill in the art will recognize many alternatives, the present invention contemplates the use of a solid state drive 61, which, as will be appreciated by those of ordinary skill in the art, is not only very rugged and shock resistant, but is also beneficially a low power storage device. This latter feature, of course, is particularly advantageous for operation of the interface pressure monitoring system 50 of the present invention on battery power such as may be required in the event of a primary power failure or in connection with a wheelchair 12.

Figures 8A, 8B:
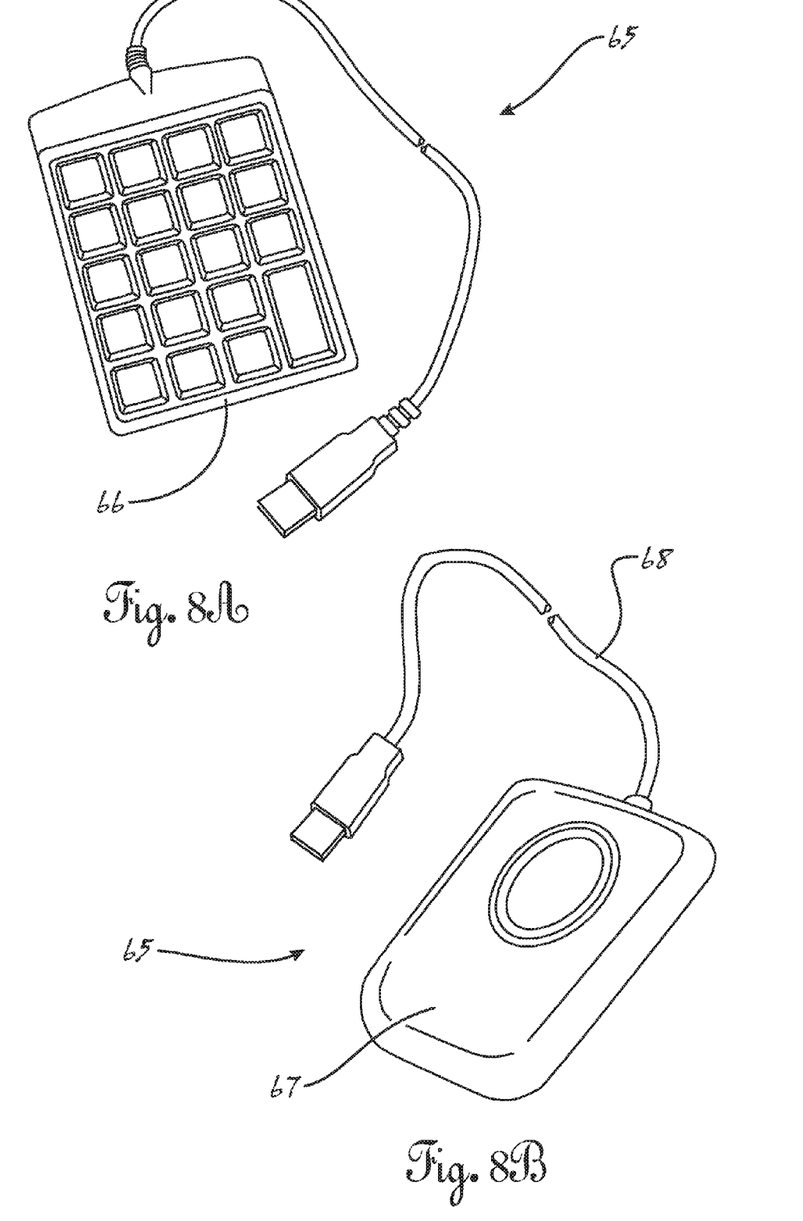
FIG. 8A shows, in a perspective view, a first user input device such as may be employed in connection with at least one preferred embodiment of the present invention.
FIG. 8B shows, in a perspective view, a second user input device such as may be employed in connection with at least one preferred embodiment of the present invention.

Still further, the processor 55 comprises a user interface 62, which particularly includes at least a graphic display device 72. Additionally, however, the user interface 62 for the processor 55 preferably comprises one or more input and or input/output devices. For example, the user interface 62 may comprise a universal serial bus ("USB") controller 63 and one or more USB ports 64 for the connection of one or more external devices 65; an integrated card reader 73; an integrated biometric input device 69 such as, for example, a fingerprint reader; and/or an aural output device 70 such as, for example, an audio speaker 71, piezoelectric tone generator or the like. As shown in FIGS. 8A and 8B, respectively, appropriate external input devices 65 for use in connection with the present invention may comprise, for example, a USB keypad 66 or a USB fingerprint reader 67. In the case of the externally provided USB fingerprint reader 67, however, it is noted that the most preferred implementation of the present invention contemplates utilization of such a reader 67 as comprises a sufficiently long cable 68 as to enable utilization of the reader 67 for collection of biometric identification data from the bedridden or wheelchair bound patient 10.

Figure 6A:
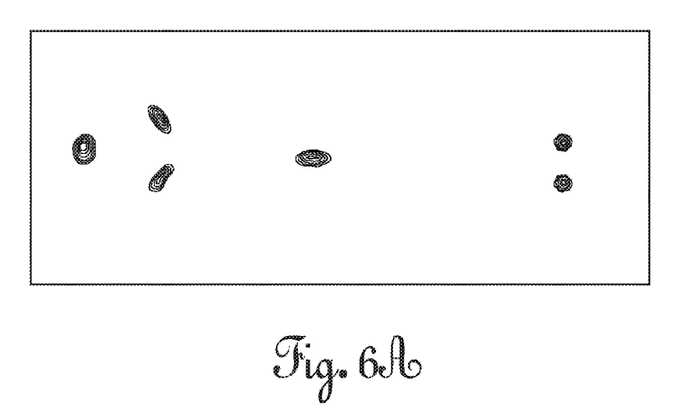
FIG. 6A shows, in a schematic representation, a first representative mapping of patient interface pressures as detected and utilized by the present invention for determining the necessity of an intervention.
Figure 6B:
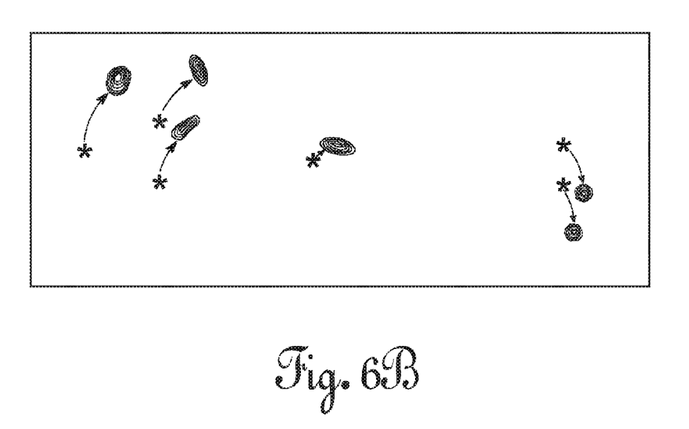
FIG. 6B shows, in a schematic representation, a second representative mapping of patient interface pressures as detected and utilized by the present invention for determining the necessity of an intervention.
Figure 6C:
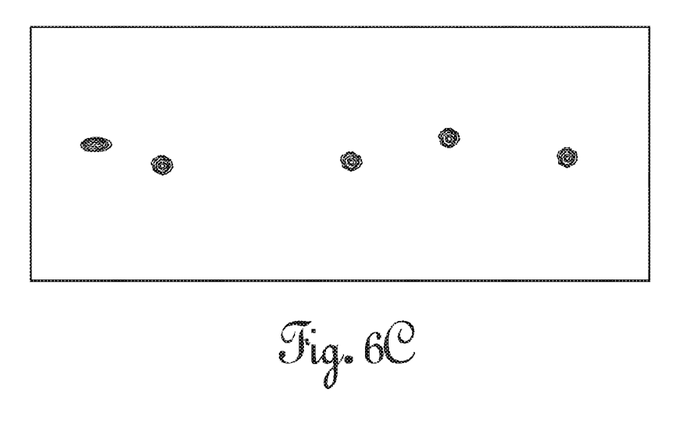
FIG. 6C shows, in a schematic representation, a third representative mapping of patient interface pressures as detected and utilized by the present invention for determining the necessity of an intervention.

In any case, and turning additionally to FIGS. 6A through 6C, the operation of the interface pressure monitoring system 50 of the present invention is described. With the patient 10 resting adjacent the underlayment 51 as previously described, the pressure sensors 52 of the underlayment detect areas of relatively high pressure as may be expected in the regions of bony prominences as discussed in the background hereto. The detected pressure data is then transmitted to the processor 55 through the data acquisition circuit 56 where under the control of the controller 59 and associated firmware and/or software, the acquired data is time-stamped and mapped to its source location in the underlayment 51 and stored in the provided mass storage device 60.

Based upon the mapping of the data, the controller 59 if possible determines the body position of the patient 10. For example, the pressure data as depicted in conceptual mapping of FIG. 6A clearly indicates a patient 10 lying atop the underlayment in the supine position. Given such a determination, the controller 59 is then able to recognize that the pressure data as depicted in the conceptual mapping of FIG. 6B represents only a migration of the patient 10 across the underlayment 51 as opposed to an actual repositioning of the patient 10. In this manner, the controller 59 is adapted to treat a transition from the state of FIG. 6A to the state of FIG. 6B (or the like) as if the patient has had no relief from the interface pressure.

In any case, the controller 59 is further adapted to monitor the length of time that the patient 10 remains in such a substantially unchanged position and, upon the expiration of a threshold length of time to signal, through the aural output device 70, a wired or wireless Ethernet connection or the like, that a caregiver should attend to the repositioning of the patient 10. If the caregiver does not respond in a timely fashion, however, the controller 59 may also be adapted to send an alarm to a supervisor or other authority. In any case, the controller 59 and associated mass data storage device 60 is preferably adapted to maintain an audit record of the pressures experienced over time by the patient 10 as well as the interventions received by the patient 10. To this end, the processor 50 may be adapted to require identification of the caregiver and/or the patient 10 prior to or upon the taking of an action respecting the care of the patient. In implementation of this feature, the previously described keypad 65, fingerprint readers 67, 69 and/or integrated card reader 73 may be conventionally utilized.

Referring then to FIG. 6C, however, it may be that the patient 10 is partially ambulatory or that it is desired that the controller 59 autonomously determine an adequate repositioning of the patient 10. In any such case, the controller 59 is adapted to "reset" to zero the tracked time in position of the patient 10. To this end, the previously discussed body position determination feature of the present invention may be utilized to determine that, as depicted in the conceptual mapping of FIG. 6C, the patient has been rolled into the left side lateral position.

Figure 7A:
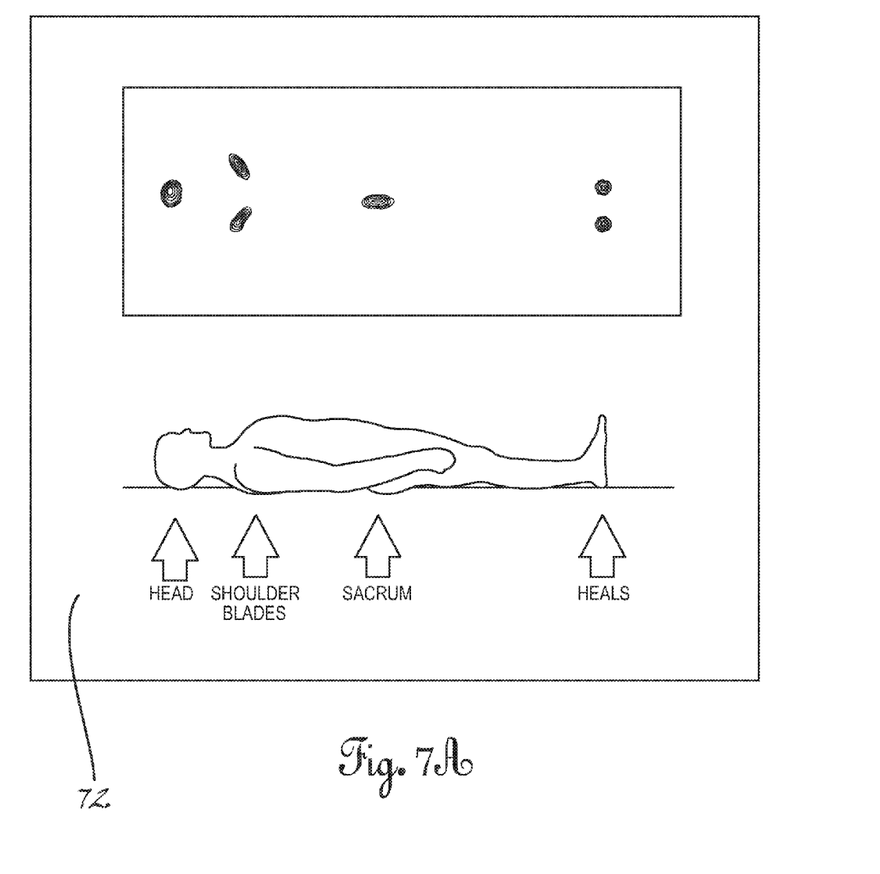
FIG. 7A shows, in a screen capture view, a first representative graphical display as generated according to the preferred method of use of the present invention for the conveyance of useful information to a patient and/or caregiver.
Figure 7B:
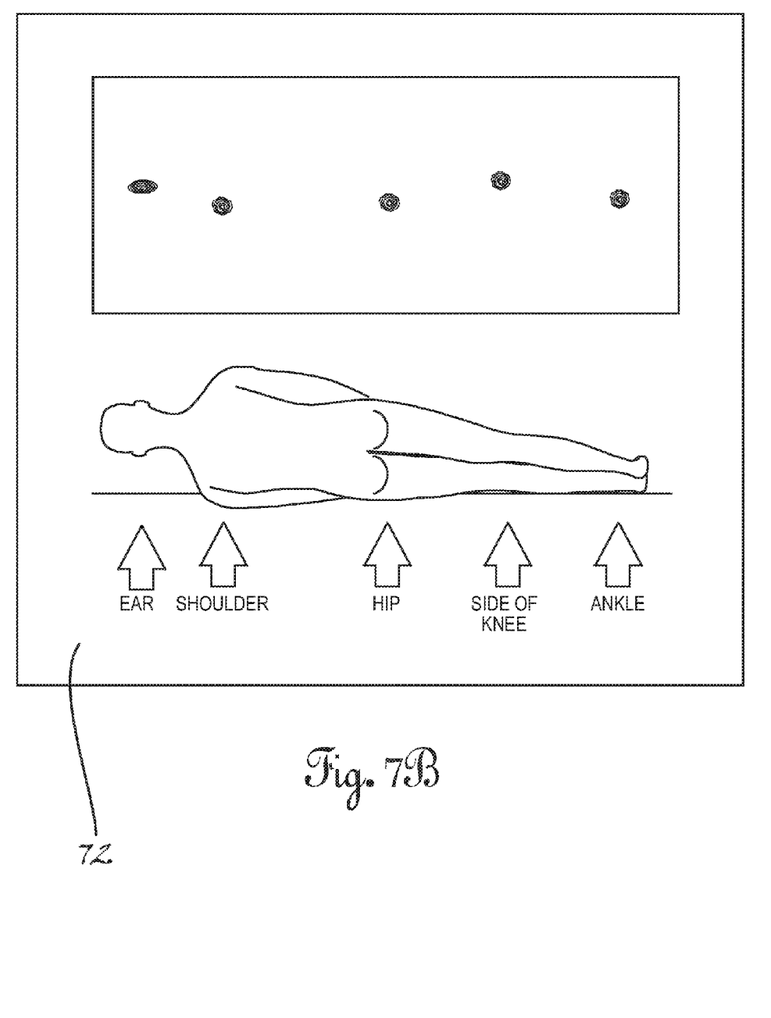
FIG. 7B shows, in a screen capture view, a second representative graphical display as generated according to the preferred method of use of the present invention for the conveyance of useful information to a patient and/or caregiver.

Referring further still to FIGS. 7A and 7B, it is shown that the described body position determination feature is also particularly advantageous in providing an image through the display 72 that may be readily interpreted by a layperson in the role of caregiver. As shown in the figures, the display preferably shows an overhead view of the pressure mapping of the underlayment 51 as well as a plain language indication of the locations of heighten pressures as determined by the controller 59. These displays may then be used by the layperson caregiver to doubly ensure proper care of the patient 10.

While the foregoing description is exemplary of the preferred embodiment of the present invention, those of ordinary skill in the relevant arts will recognize the many variations, alterations, modifications, substitutions and the like as are readily possible, especially in light of this description, the accompanying drawings and claims drawn thereto. For example, those of ordinary skill in the art will recognize, in light of this exemplary description, that the keypad 65, fingerprint readers 67, 69 and/or integrated card reader 73 are preferably utilized to "lock out" a supervisory role such that the stored patient care data may not be nefariously tampered with. Likewise, those of ordinary skill in the art will recognize that appropriate safety measures should be incorporated into any particular implementation, including, for example, waterproofing measures and other electrical safety measures such as interference shielding.

Additionally, those of ordinary skill in the art will recognize that the system and methods described herein for the prevention, treatment and cure of decubitus ulcers may be applied to similar ends such as, for example, for ensuring that newborn babies are rotated on appropriate schedules, thereby preventing cranial deformations concomitant immobility during the period of fusion of the cranial joints. In any case, because the scope of the present invention is much broader than any particular embodiment, the foregoing detailed description should not be construed as a limitation of the scope of the present invention, which is limited only by the claims appended hereto.

What is claimed is:

1. A system for monitoring localized interface pressures produced between a surface and a patient supported thereon, said monitoring system comprising:
   an underlayment adapted to be interposed between a patient support surface and a patient resting adjacent said patient support surface, said underlayment comprising a plurality of pressure sensors; and
   a processor in electrical communication with said pressure sensors of said underlayment, said processor being adapted to:
      acquire and map pressure data as measured by said pressure sensors;
      store said mapped pressure data;
      analyze said stored pressure data for the determination of the body position of the patient from the group consisting of:
         the supine position;
         the prone position; and
         a lateral position;
      determine, based upon whether the determined body position of the patient has remained unchanged, from one said body position to another said body position, over a length of time exceeding an established threshold value, whether repositioning of the patient should take place;

generate a graphical image of said mapped pressure data, wherein said graphical image comprises a written language identification of the regions of the body of the patient that are placed at heightened risk for tissue breakdown as a result of the determined body position of the patient remaining unchanged over a length of time exceeding said established threshold value; and display, through a user interface, said graphical image.

2. The monitoring system as recited in claim 1, wherein said pressure sensors comprise piezoelectric sensors.

3. The monitoring system as recited in claim 2, wherein said piezoelectric sensors are arranged in a sensor array.

4. The monitoring system as recited in claim 1, wherein said patient support surface comprises a mattress.

5. The monitoring system as recited in claim 1, wherein said processor is further adapted to receive, through a user interface, an adjustment determined by a caregiver based upon patient risk factors to said established threshold value.

6. The monitoring system as recited in claim 1, wherein said processor is further adapted to reset said length of time to zero in response to manual input.

7. A system for monitoring localized interface pressures produced between a surface and a patient supported thereon, said monitoring system comprising:

an underlayment adapted to be interposed between a patient support surface and a patient resting adjacent said patient support surface, said underlayment comprising a plurality of pressure sensors; and a processor in electrical communication with said pressure sensors of said underlayment, said processor being adapted to:

acquire and map pressure data as measured by said pressure sensors;

store said mapped pressure data;

analyze said stored pressure data for the determination of the body position of the patient from the group consisting of:
the supine position;
the prone position; and
a lateral position;

determine, based upon whether the determined body position of the patient has remained unchanged, from one said body position to another said body position, over a length of time exceeding an established threshold value, whether repositioning of the patient should take place;

transmit a signal indicating a need for caregiver intervention upon the determined body position of the patient remaining unchanged over a length of time exceeding said established threshold value;

generate a graphical image of said mapped pressure data, wherein said graphical image comprises a written language identification of the regions of the body of the patient that are placed at heightened risk for tissue breakdown as a result of the determined body position of the patient remaining unchanged over a length of time exceeding said established threshold value; and display, through a user interface, said graphical image.

8. The monitoring system as recited in claim 7, wherein said pressure sensors comprise piezoelectric sensors.

9. The monitoring system as recited in claim 8, wherein said piezoelectric sensors are arranged in a sensor array.

10. The monitoring system as recited in claim 7, wherein said patient support surface comprises a mattress.

11. The monitoring system as recited in claim 7, wherein said processor is further adapted to create and store an audit record recording time spent by the patient in a determined body position.

12. The monitoring system as recited in claim 7, wherein said processor is further adapted to create and store an audit record recording time spent by the patient in a determined body position prior to intervention by a caregiver and the identity of the caregiver making the intervention.

13. The monitoring system as recited in claim 12, said monitoring system further comprising a keypad and wherein said keypad and said processor are cooperatively adapted to capture the identity of the caregiver making the intervention.

14. The monitoring system as recited in claim 13, wherein said keypad and said processor are further cooperatively adapted to capture the identity of the caregiver making the intervention by entry of a code through said keypad.

15. The monitoring system as recited in claim 12, said monitoring system further comprising a fingerprint reader and wherein said fingerprint reader and said processor are cooperatively adapted to capture the identity of the caregiver making the intervention.

16. The monitoring system as recited in claim 15, wherein said fingerprint reader and said processor are further cooperatively adapted to capture the identity of the caregiver making the intervention by capture of a fingerprint.

17. The monitoring system as recited in claim 12, said monitoring system further comprising a card reader and wherein said card reader and said processor are cooperatively adapted to capture the identity of the caregiver making the intervention.

18. The monitoring system as recited in claim 17, wherein said card reader and said processor are further cooperatively adapted to capture the identity of the caregiver making the intervention by reading of an identification card.

19. The monitoring system as recited in claim 7, wherein said processor is further adapted to transmit, upon passage of an established time following transmission of said signal indicating a need for caregiver intervention, an alarm signal indicating untimely caregiver intervention.

20. The monitoring system as recited in claim 7, wherein said processor is further adapted to receive, through a user interface, an adjustment determined by a caregiver based upon patient risk factors to said established threshold value.

21. The monitoring system as recited in claim 7, wherein said processor is further adapted to create and store an audit record recording time spent by the patient in a determined body position, time spent by the patient in a determined body position prior to intervention by a caregiver and the identity of the caregiver making the intervention.

* * * * *